United States Patent [19]
Sorabella et al.

[11] Patent Number: 5,624,617
[45] Date of Patent: Apr. 29, 1997

[54] METHOD OF MANUFACTURE FOR CATHETER LUMEN LUBRICITY

[75] Inventors: Robert W. Sorabella, Boston; Daniel O. Lausten, Danvers, both of Mass.

[73] Assignee: Medtronic, Inc., Minneapolis, Minn.

[21] Appl. No.: 366,942

[22] Filed: Dec. 30, 1994

[51] Int. Cl.$^6$ .................................................. B29C 47/06
[52] U.S. Cl. .......................... 264/103; 264/136; 264/149; 264/150; 264/171.12; 264/171.26; 264/173.19; 264/300
[58] Field of Search ..................... 264/103, 173.19, 264/171.26, 149, 150, 300, 130, 171.12, 136

[56] References Cited

U.S. PATENT DOCUMENTS

| | | | |
|---|---|---|---|
| 4,100,309 | 7/1978 | Micklus | 427/2 |
| 4,119,094 | 10/1978 | Micklus | 128/132 R |
| 4,299,256 | 11/1981 | Bacehowski et al. | 264/300 |
| 4,321,226 | 3/1982 | Markling | 264/149 |
| 4,516,972 | 5/1985 | Samson | 604/282 |
| 4,529,614 | 7/1985 | Burns | 427/2 |
| 4,636,346 | 1/1987 | Gold et al. | 264/149 |
| 4,720,521 | 1/1988 | Spielvogel | 524/862 |
| 4,898,591 | 2/1990 | Jang et al. | 604/282 |
| 4,904,431 | 2/1990 | O'Maleki | 264/149 |
| 4,904,433 | 2/1990 | Williamitis | 264/130 |
| 4,945,126 | 7/1990 | Crosby | 524/507 |
| 5,045,071 | 9/1991 | McCormick et al. | 604/280 |
| 5,061,424 | 10/1991 | Karimi et al. | 264/300 |
| 5,061,738 | 10/1991 | Solomon | 523/100 |
| 5,078,702 | 1/1992 | Pomeranz | 604/280 |
| 5,084,315 | 1/1992 | Karimi | 428/36.6 |
| 5,137,672 | 8/1992 | Fujiu et al. | 264/300 |
| 5,143,963 | 9/1992 | Sterling | 524/366 |
| 5,227,080 | 7/1993 | Berry | 138/105 |
| 5,254,107 | 10/1993 | Soltesz | 604/282 |
| 5,266,359 | 11/1993 | Spielvogel | 427/388.4 |
| 5,370,899 | 12/1994 | Conway et al. | 264/130 |
| 5,451,209 | 9/1995 | Ainsworth et al. | 604/96 |

FOREIGN PATENT DOCUMENTS

| | | |
|---|---|---|
| 0520692 | 6/1992 | European Pat. Off. |
| 9400176 | 1/1994 | WIPO |

*Primary Examiner*—Jeffery R. Thurlow
*Attorney, Agent, or Firm*—Dianne M. F. Plunkett; Harold R. Patton

[57] ABSTRACT

A method of manufacture is disclosed for a PTCA guiding catheter. The catheter includes a lamination of an inner structural polymer tube, a lubricating means disposed on the inside of the inner structural polymer tube, a reinforcement means embedded at least partially within the inner structural polymer tube, and an outer structural polymer tube embedded at least partially within the reinforcement means and fused at least partially to the inner structural polymer tube. The method of manufacture includes the steps of forming a core polymer into a solid shape, the core polymer including a base polymer and a lubricating means, forming a layer of an inner structural polymer tube over at least a portion of the core polymer such that the lubricating means leaches to the inner structural polymer tube, forming a reinforcement means over at least a portion of the inner structural polymer tube, forming a layer of an outer structural polymer tube over at least a portion of the reinforcement means, and separating the inner structural polymer tube from the core polymer.

18 Claims, 5 Drawing Sheets

METHOD OF MANUFACTURE FOR CATHETER LUMEN LUBRICITY

FIELD OF THE INVENTION

The present invention relates to an article and a method of manufacture for a catheter.

BACKGROUND OF THE INVENTION

Catheters are tube-like members which are inserted into the body for diagnostic or therapeutic reasons. One of the therapeutic procedures applicable to the present invention is known as percutaneous transluminal coronary angioplasty ("PTCA"). PTCA can be used, for example, to reduce arterial buildup of cholesterol fats or atherosclerotic plaque. Catheters must have sufficient bending stiffness, kink resistance, and torsional rigidity to provide structural integrity for the catheter. The catheter must also be fluoroscopically visible or radiopaque so that the physician's catheter manipulation through the vasculature is facilitated. Further, it is necessary for the catheter, particularly the inner layer or "liner", to exhibit lubricity so that therapeutic devices can be easily passed through the catheter.

U.S. Pat. No. 5,061,738, issued to Solomon et al., discloses a medical article having a coating of an anticoagulant and a lubricant. The preferred lubricant is a non-curing silicone such as a polydialkylsiloxane. An antithrombogenic agent such as heparin is mixed with the lubricant and the mixture is then dissolved in a solvent. The medical article is immersed in the resulting composition of the antithrombogenic agent, the lubricant, and the solvent to coat the article. In the case where the article is a catheter, the lumen wall is coated by drawing the composition into the lumen by application of reduced pressure.

U.S. Pat. No. 5,084,315, issued to Karimi et al., discloses an article which becomes lubricious when wet which includes a base polymer and a coating composition. The coating composition is comprised of a lubricating polymer and a matrix polymer where the matrix polymer is selected so that it adheres to the base polymer and serves as a carrier for the lubricating polymer. The lubricating polymer is selected from a group of polymers which absorb water and are known as hydrophilics. A method of manufacturing is also disclosed where the base polymer and the coating composition are coextruded so that the coating composition is laminated on the surface of the base polymer.

U.S. Pat. No. 4,945,126, issued to Crosby et al., discloses a method of manufacture of a lubricant system which consists of a polymer matrix and a lubricant which comprises a blend of a polyolefin and finely divided polytetrafluoroethylene. The method involves the melt mixing of the polymer matrix and a lubricant using a process such as extrusion.

U.S. Pat. No. 5,254,107 issued to Soltesz, discloses a catheter comprising an inner plastic layer, a braided stainless steel fiber tubular member surrounding the inner plastic layer, and an outer tubular plastic layer. The braided stainless steel fiber tubular member is completely embedded in the outer tubular plastic layer along the length of the catheter.

It is an object of the invention to achieve catheter lubricity while providing structural integrity by providing a uniform coating of a lubricating polymer to the inner surface of the liner of the catheter such that bonding between the outer surface of the liner and adjacent layers is not compromised.

It is a further object of the invention to provide large inside diameters and correspondingly smaller wall thicknesses. What is needed is a catheter with a construction which provides the requisite structural integrity and lubricity while allowing a larger inside diameter.

SUMMARY OF THE INVENTION

One aspect of the present invention is an article of manufacture, preferably a PTCA guiding catheter. The catheter comprises an inner structural polymer tube, which defines at least one lumen, a lubricating polymer, located principally on the inner surface of and bonded to the inner structural polymer tube, a reinforcement member, embedded at least partially within the inner structural polymer tube, and an outer structural polymer tube, whereby the outer structural polymer tube is embedded at least partially within the reinforcement member and fused at least partially to the outer surface of the inner structural polymer tube. The catheter provides an improved multi-layer design over prior art catheters which employ distinct layers for lubricity and structural integrity where such layers are comprised of materials which are generally not melt compatible with each other. Because the materials selected for the inner and outer structural polymer tubes are melt compatible, the two materials can be intimately fused together to provide an encapsulation of the reinforcement member.

An alternative embodiment is a liner for a PTCA guiding catheter which comprises an inner structural polymer tube, which defines at least one lumen, and a lubricating polymer, located principally on the inner surface of and bonded to the inner structural polymer tube. The liner can then be processed into a complete catheter using techniques known in the art or used in combination with a plurality of liners to comprise a multi-lumen catheter.

An additional aspect of the invention is a method of manufacturing a PTCA guiding catheter. The method comprises the steps of forming a core polymer into a solid shape, the core polymer including a base polymer and a lubricating polymer, forming a layer of an inner structural polymer tube over at least a portion of the core polymer such that the lubricating polymer leaches from the core polymer to the inner structural polymer tube, forming a reinforcement member over at least a portion of the inner structural polymer tube, whereby the reinforcement member is embedded at least partially within the inner structural polymer tube, forming a layer of an outer structural polymer tube over at least a portion of the reinforcement member, whereby the outer structural polymer tube is embedded at least partially within the reinforcement member and fused at least partially to the outer surface of the inner structural polymer tube, and separating the inner structural polymer tube from the core polymer.

A futher aspect of the invention is a method of manufacturing a liner for a PTCA guiding catheter, which comprises the steps of forming a core polymer into a solid shape, the core polymer including a base polymer and a lubricating polymer, forming a layer of an inner structural polymer tube over at least a portion of the core polymer such that the lubricating polymer leaches from the core polymer to the inner structural polymer tube, and separating the inner structural polymer tube from the core polymer.

DETAILED DESCRIPTION OF THE PREFERRED EMBODIMENTS

Figure 3:
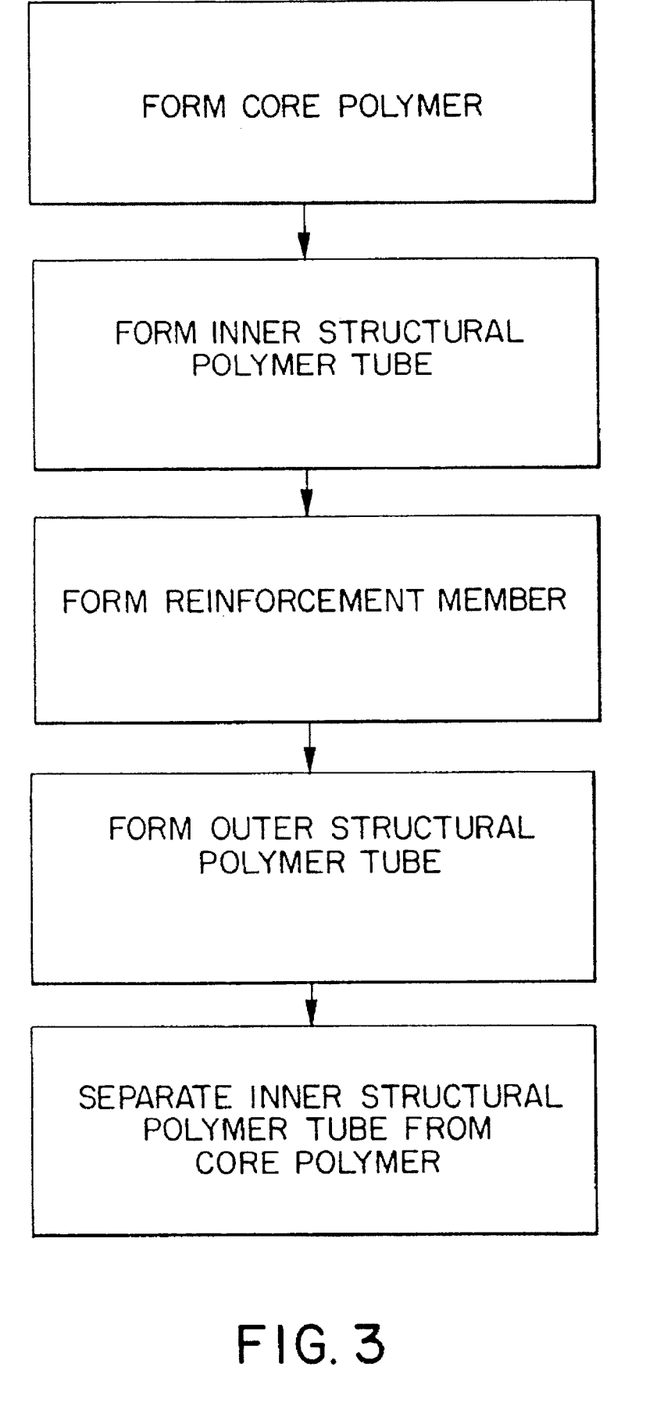
FIG. 3 shows the method of the invention.

One aspect of the invention is a method of manufacturing a PTCA guiding catheter comprising the following steps. Refer to FIG. 3. A core polymer, which comprises a base polymer and a lubricating polymer, is prepared by a two step process. The first step involves a melt blending of a lubricating polymer, preferably polydimethylsiloxane (PDMS) at a concentration of 10–30% by weight and preferably, 20%, as well as an acetal copolymer, preferably a polyoxymethylene copolymer, at a concentration of 90–70% and preferably, 80%. The compound produced by the first step is known by the tradename and formula GELCON® LW90-SC, obtainable from the Hoechst Celanese Corporation, Chatham, N.J.

The second step involves a melt blending of the compound formed by the first step, at a preferred PDMS concentration of 1.5–2% by weight, and an acetal copolymer, preferably a polyoxymethylene copolymer such as ULTRAFORM®, obtainable from BASF Corporation, Wyandotte, Mich., at a preferred concentration of 98.5–98%. The resulting compound is extruded to a solid core of 1–3 mm, and preferably 1.8 mm in diameter, to form the core polymer. It is noteworthy that an alternative method combines the first and second steps into a single step with the same resulting concentrations in the core polymer. The preferred method was chosen for ease of manufacturing and cost-effectiveness.

An inner structural polymer tube is subsequently formed over at least a portion of the core polymer in an extrusion process. The inner structural polymer tube comprises a polyether block amide copolymer in the range of Shore durometer D65–D75, preferably D70 7033 PEBAX®, obtainable from the Elf Atochem Corporation, Philadelphia, Pa., at a concentration of 84.5–73.5% and preferably, 79%, bismuth subcarbonate, at a concentration of 15–25% by weight and preferably 20%, and titanium dioxide, at a concentration of 0.5–1.5% and preferably 1%. The bismuth subcarbonate, a commonly used radiopaque additive for polymers, can be obtained from HEK-Gmbh, Germany while the titanium dioxide, a commonly used pigment, can be obtained from the E.I. Du Pont de Nemours & Company, Wilmington, Del.

During the extrusion of the inner structural polymer tube, the compound comprising the inner structural polymer tube is plasticated in the barrel and crosshead region of the extruder while the core polymer is drawn through the crosshead die. The crosshead is maintained at a temperature of approximately 440 degrees to 465 degrees F. Under the heat and pressure in the crosshead die, the core polymer is softened and undergoes a partial phase transformation which liberates the PDMS lubricating polymer to the outer surface of the core polymer. Simultaneously, a homogeneous melt of the compound comprising the inner structural polymer tube is obtained in the crosshead. This compound is formed around the core polymer and leaches the PDMS from the core polymer. The leaching is believed to be assisted by the phase transformations during extrusion and also from the frictional energy at the interface of the inner structural polymer tube and the core polymer. The preferred resulting cross-sectional geometry for the inner structural polymer tube is an annulus which is concentric with the core polymer, of a preferred wall thickess of 0.0025 inches.

Following the extrusion and subsequent cooling of the inner structural polymer tube and core polymer assembly, the core polymer may be separated from the inner structural polymer tube or, alternatively, the core polymer may be used to support the inner structural polymer tube for subsequent continuous processing. The separation of the core polymer from the inner structural polymer tube and lubricating polymer results in the inner layer or "liner" of a catheter which can be used as a subassembly for individual guide catheter construction using methods and materials which are well known in the art.

If subsequent continuous processing is desired, the assembly can be subsequently braided with a stainless steel wire reinforcement member using a braiding machine such as those Obtainable from the Wilhelm Steeger GmbH & Co., Germany, and then overextruded with an outer structural polymer tube of a polyether block amide copolymer in the range of Shore durometer D65–D75, preferably D70 7033 PEBAX®, which is melt compatible with the inner structural polymer tube. The core polymer can then be separated from the laminated catheter assembly of the lubricating polymer, the inner structural polymer tube, the reinforcement member, and the outer structural polymer tube.

The respective layers of the catheter must be integrally laminated for the catheter to exhibit acceptable performance. It is critical that the outer structural polymer tube be fused at least partially to the outer surface of the inner structural polymer tube and be embedded at least partially within the reinforcement member. Further, it is desired to have the reinforcement member embedded at least partially within the inner structural polymer tube. The forgoing are necessary to achieving the requisite bending stiffness, kink resistance, and torsional rigidity for the catheter. Extrusion pressures of approximately 750 psi and a preheat temperature of approximately 500 degrees F. are required to achieve the desired lamination of the respective layers of the catheter.

Figure 1:
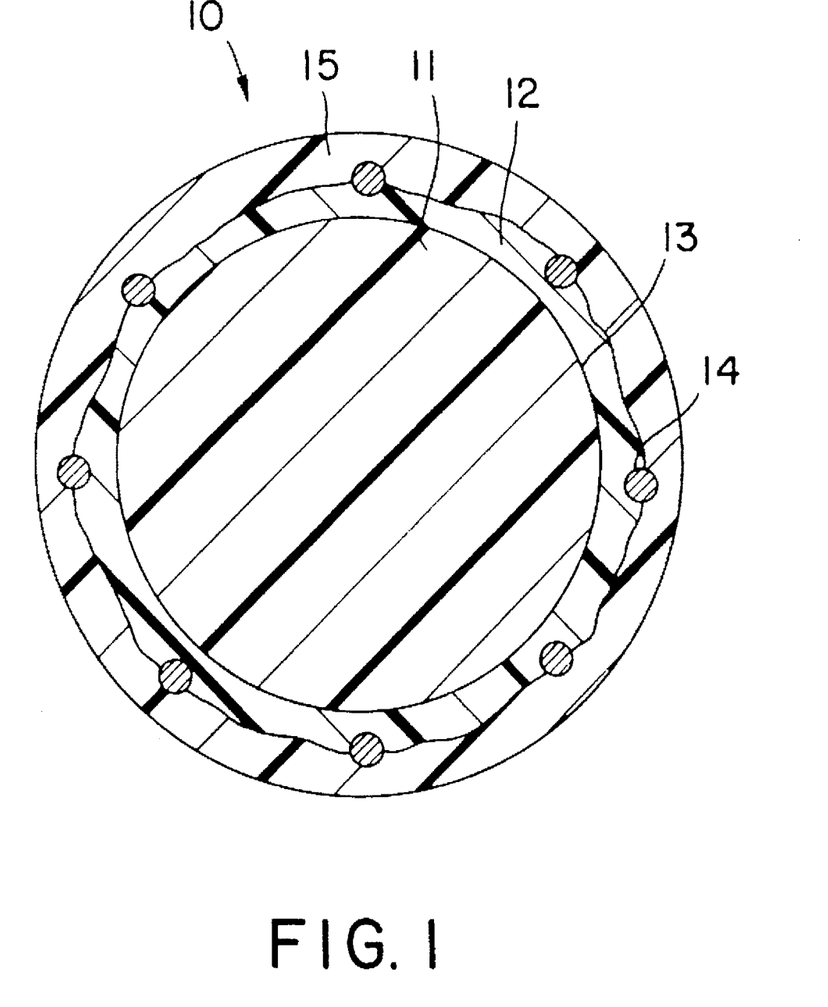
FIG. 1 shows a cross-section of the catheter shaft showing the core polymer, the inner structural polymer tube, the lubricating polymer, the reinforcement member, and the outer structural polymer tube.

FIG. 1 illustrates the preferred embodiment of the invention, a PTCA guiding catheter assembly 10. The core polymer 11 is extruded to a generally circular cross-section of approximately 1.8 mm in diameter. The inner structural polymer tube 12 is extruded over the core polymer 11. During the extrusion process, the PDMS lubricating polymer 13 leaches from the core polymer 11 to the inner structural polymer tube 12. The assembly of the core polymer 11, the inner structural polymer tube 12 and the PDMS lubricating polymer 13 is subsequently braided with a stainless steel wire reinforcement member 14. An outer structural polymer tube 15 is then extruded over the assembly comprising the core polymer 11, the inner structural polymer tube 12, the PDMS lubricating polymer 13, and the stainless steel wire reinforcement member 14. The core polymer 11 is then removed.

Bonding between the repective layers of the catheter is critical to achieving the requisite torsional stiffness and kink resistance for the catheter. It is therefore essential that the PDMS lubricating polymer be primarily concentrated on the inner surface of the liner. The concentration on the inner surface must not, however, rise to the level of a buildup of PDMS. A buildup restricts the lumen of the liner, making the manipulation of therapeutic devices more difficult and it is possible that PDMS will be expelled into the vasculature as the result of the interface of therapeutic devices with the liner. Using the applicants method, the PDMS is primarily concentrated on the inner surface of the liner because of the leaching which occurs at the inner surface of the liner from the core polymer. Also, buildup of PDMS is minimized because the heat and pressure in the crosshead of the extruder forces the inner structural polymer robe into intimate encapsulation of the core polymer.

Figure 2A:
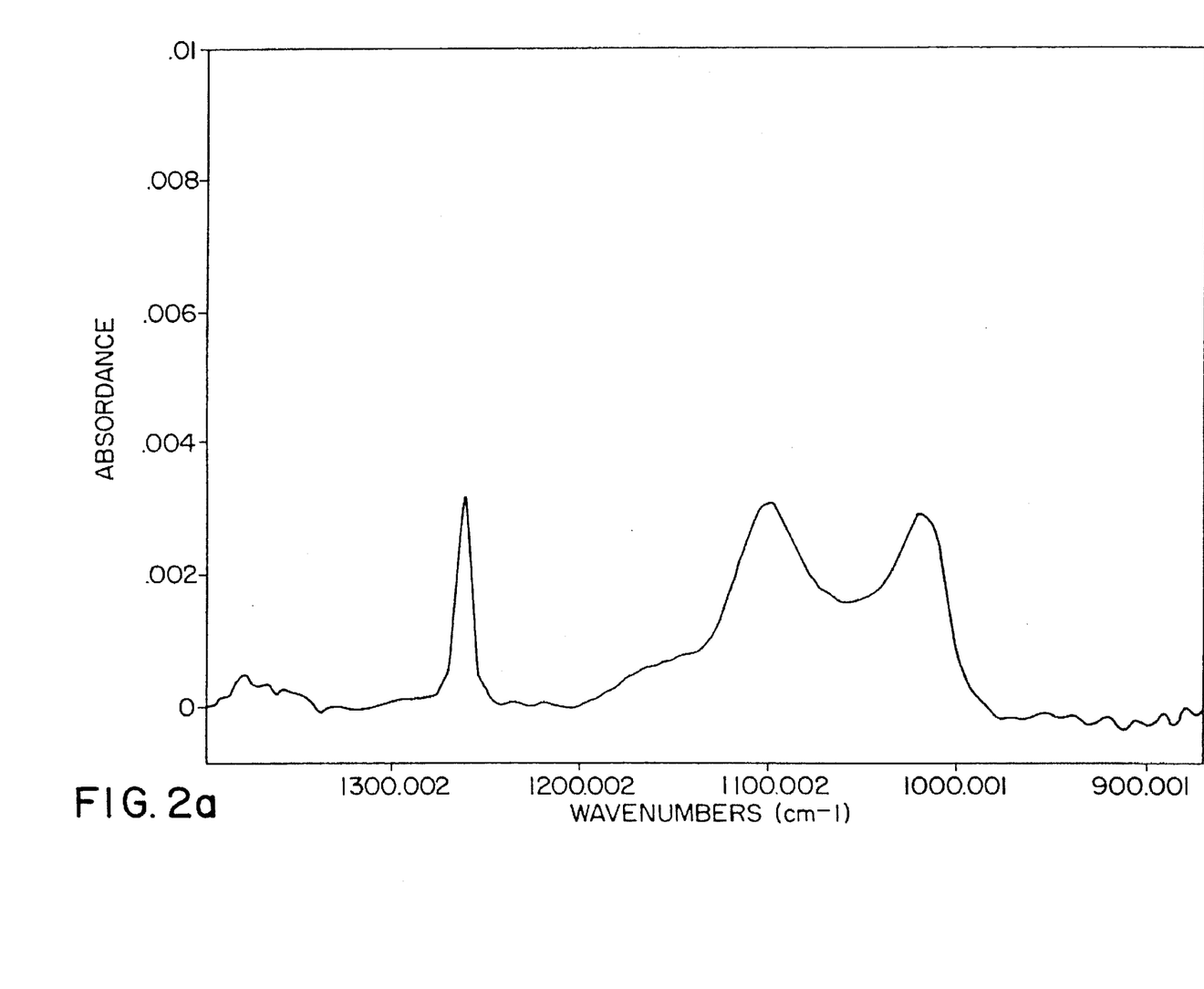
FIG. 2a shows the results of Fourier Transform Infrared Spectroscopy ("FTIR") testing on the preferred embodiment as it is applied to the liner of the catheter shaft. The test sample was removed from the inner surface of the liner of the catheter shaft. The FTIR results indicate the presence of polydimethylsiloxane (PDMS) as evidenced by the appearance of Si-CH$_3$ and Si-O-Si peaks at wavenumbers between 1200–1300 cm$^{-1}$ and 1000–1100 cm$^{-1}$.
Figure 2B:
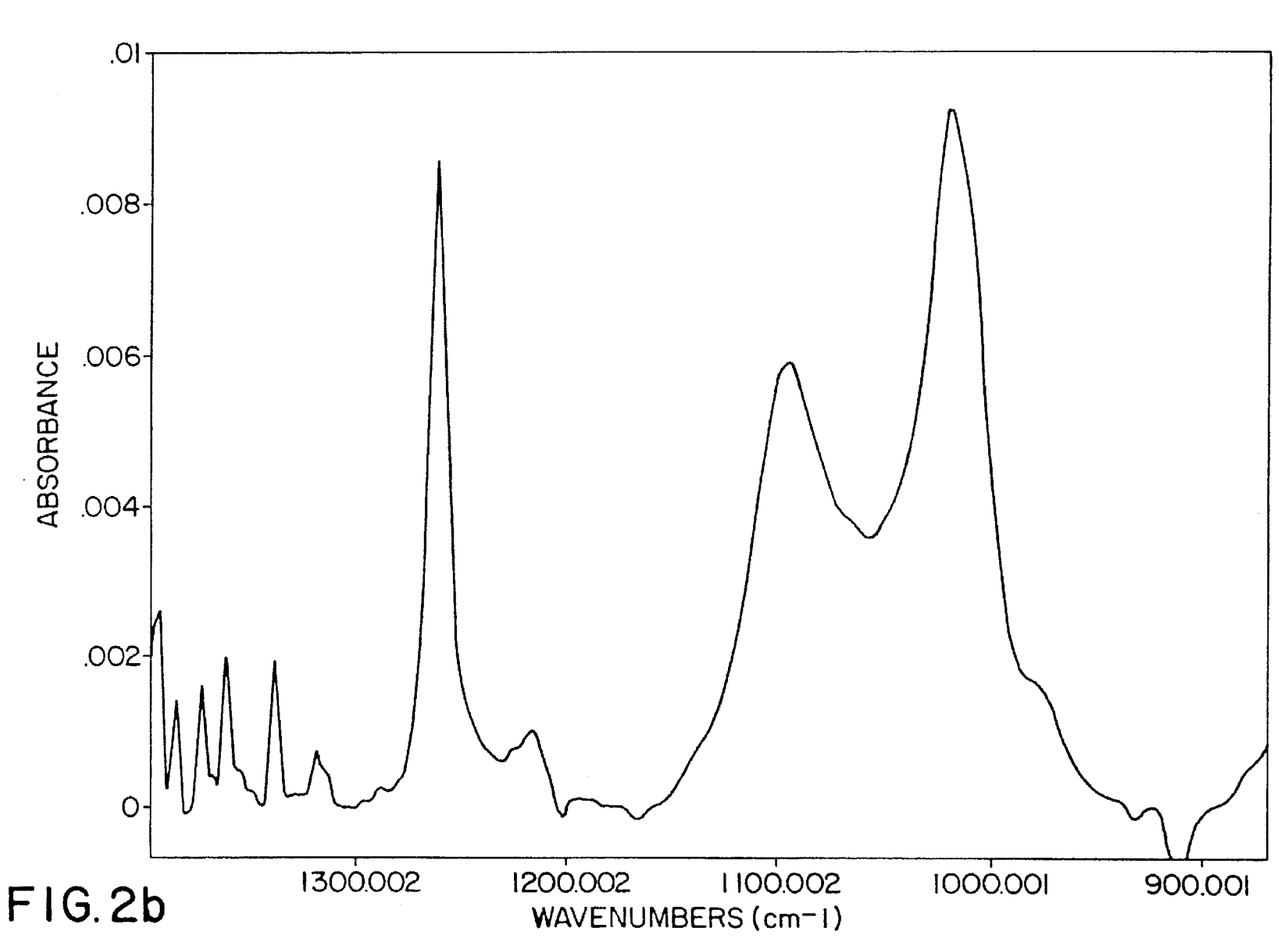
FIG. 2b shows the results of FTIR testing on a control sample of PDMS. The FTIR results indicate the presence of polydimethylsiloxane as evidenced by the appearance of Si-CH$_3$ and Si-O-Si peaks at wavenumbers between 1200–1300 cm$^{-1}$ and 1000–1100 cm$^{-1}$.
Figure 2C:
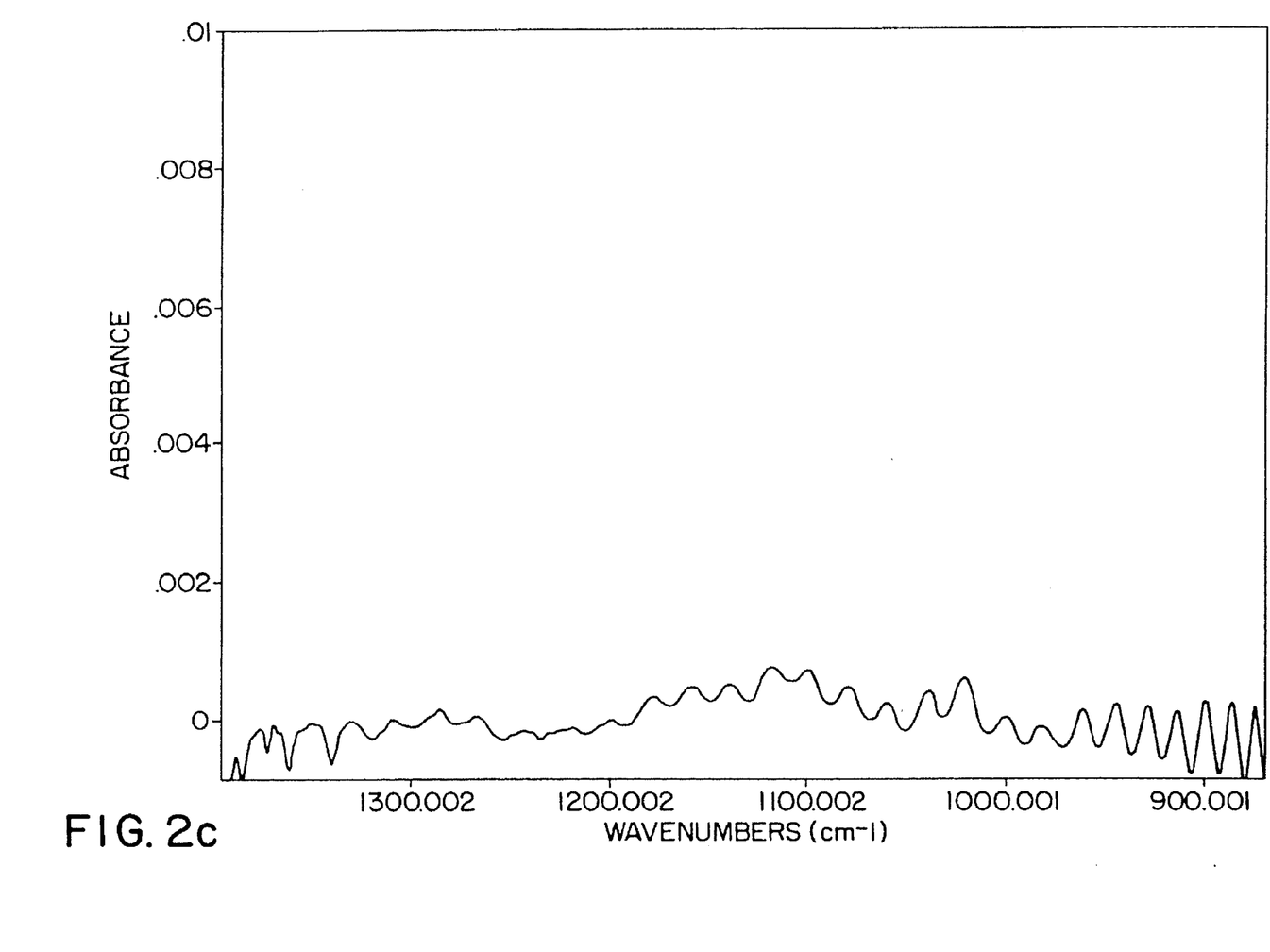
FIG. 2c shows the FTIR testing results for the 0.5% concentration of the first compound in the second compound. The 0.5% concentration, which is lower than that of the preferred embodiment, was applied to the liner of the catheter shaft. The test sample was removed from the inner surface of the liner of the catheter shaft. The FTIR results show no discernable presence of PDMS, as evidenced by the absence of Si-CH$_3$ and Si-O-Si peaks at wavenumbers between 1200–1300 cm$^{-1}$ and 1000–1100 cm$^{-1}$.

A preferred PDMS concentration of 1.5–2.0% in the core polymer results in a measurable concentration of PDMS on the inner surface of the liner of the catheter. FIG. 2a shows the result of Fourier Transform Infrared Spectroscopy ("FTIR") testing on the preferred embodiment. The FTIR results indicate the appearance of Si-$CH_3$ and Si-O-Si peaks at wavenumbers between 1200–1300 $cm^{-1}$ and 1000–1100 $cm^{-1}$, respectively. The results shown in FIG. 2a correlate with those of a control sample, shown in FIG. 2b, which indicates the appearance of Si-$CH_3$ and Si-O-Si peaks at wavenumbers between 1200–1300 $cm^{-1}$ and 1000–1100 $cm^{-1}$, respectively. In contrast, FTIR testing of 0.5% PDMS concentration in the core polymer produced no discernible presence of PDMS on the inner surface of the liner of the catheter. This result is shown in FIG. 2c.

The preceding specific embodiments are illustrative of the practice of the invention. It is to be understood, however that other expedients known to those skilled in the art or disclosed herein, may be employed without departing from the spirit of the invention or the scope of the appended claims.

What is claimed is:

1. A method of manufacture for a lubricious, structurally integral liner for an intravascular catheter comprising the steps of:
   (a) forming a core polymer into a solid shape, the core polymer including a melt blend of a base polymer and a lubricating polymer, the base polymer being blended at a concentration of less than 99.5% with the lubricating polymer;
   (b) softening the core polymer under heat and pressure to the point of a partial phase change of the core polymer;
   (c) liberating the lubricating polymer to the outer surface of the core polymer;
   (d) providing a homogeneous melt of an inner structural polymer;
   (e) forming a layer of the inner structural polymer into a tube over at least a portion of the core polymer;
   (f) leaching the lubricating polymer primarily to the inner surface of the inner structural polymer tube;
   (g) integrating the inner structural polymer tube to form the intravascular catheter, and;
   (h) separating the inner structural polymer tube from the core polymer.

2. The method according to claim 1 where forming the core polymer involves an extrusion process.

3. The method according to claim 1 where the solid shape is formed to a generally circular cross-section.

4. The method according to claim 1 where forming the layer of the inner structural polymer tube involves an extrusion process.

5. The method according to claim 1 where the layer of the inner structural polymer tube is formed to a generally annular cross-section.

6. The method according to claim 1 where the base polymer is blended at a concentration of approximately 98.5–98% with the lubricating polymer.

7. The method according to claim 6 where the base polymer comprises an acetal copolymer.

8. The method according to claim 6 where the the lubricating polymer comprises a polydimethylsiloxane.

9. A method of manufacture for an intravascular catheter comprising the steps of:
   (a) forming a core polymer into a solid shape, the core polymer including a melt blend of a base polymer and a lubricating polymer, the base polymer being blended at a concentration of less than 99.5% with the lubricating polymer;
   (b) softening the core polymer under heat and pressure to the point of a partial phase change of the core polymer;
   (c) liberating the lubricating polymer to the outer surface of the core polymer;
   (d) providing a homogeneous melt of an inner structural polymer;
   (e) forming a layer of the inner structural polymer into a tube over at least a portion of the core polymer;
   (f) leaching the lubricating polymer primarily to the inner surface of the inner structural polymer tube;
   (g) forming a reinforcement member over at least a portion of the inner structural polymer tube;
   (h) softening the inner structural polymer tube under heat and pressure;
   (i) providing a homogeneous melt of an outer structural polymer which is melt compatible with the inner structural polymer;
   (j) forming a layer of the outer structural polymer into a tube over at least a portion of the reinforcement member to embed at least partially the outer structural polymer tube within the reinforcement member and the reinforcement member within the inner structural polymer tube and to fuse the outer structural polymer tube at least partially to the outer surface of the inner structural polymer tube; and
   (k) separating the inner structural polymer tube from the core polymer.

10. The method according to claim 9 where forming the core polymer involves an extrusion process.

11. The method according to claim 9 where forming the layer of the inner structural polymer tube involves an extrusion process.

12. The method according to claim 9 where the layer of the inner structural polymer tube is formed to a generally annular cross-section.

13. The method according to claim 9 where the reinforcement layer comprises braided fibers.

14. The method according to claim 9 where forming the layer of the outer structural polymer tube involves an extrusion process.

15. The method according to claim 9 where the base polymer is blended at a concentration of approximately 98.5–98% with the lubricating polymer.

16. The method according to claim 15 where the base polymer comprises an acetal copolymer.

17. The method according to claim 15 where the the lubricating polymer comprises a polydimethylsiloxane.

18. The method according to claim 9 where the solid shape is formed to a generally circular cross-section.

* * * * *

UNITED STATES PATENT AND TRADEMARK OFFICE
CERTIFICATE OF CORRECTION

PATENT NO. : 5,624,617
DATED : April 29, 1997
INVENTOR(S) : Sorabella et al.

It is certified that error appears in the above-identified patent and that said Letters Patent is hereby corrected as shown below:

Col. 6, Line 14:   "the the" should be changed to "the"

Col. 3, Line 35:   "GELCON" should be changed to "CELCON"

Col. 4, Line 18:   "thickess" should be changed to "thickness"

Col. 4, Line 33:   "Obtainable" should be changed to "obtainable"

Col. 5, Line 5:    "repective" should be changed to "respective"

Col. 5, Line 20:   "robe" should be changed to "tube"

Col. 5, Line 38:   "however" should be changed to "however,"

Signed and Sealed this

Sixth Day of January, 1998

Attest:

BRUCE LEHMAN

*Attesting Officer*          *Commissioner of Patents and Trademarks*